(12) United States Patent
Hinrikus et al.

(10) Patent No.: US 8,244,341 B2
(45) Date of Patent: Aug. 14, 2012

(54) METHOD AND DEVICE FOR DETERMINING DEPRESSIVE DISORDERS BY MEASURING BIOELECTROMAGNETIC SIGNALS OF THE BRAIN

(75) Inventors: Hiie Hinrikus, Tallinn (EE); Maie Bachmann, Saku vald (EE); Jaanus Lass, Tallinn (EE); Anna Suhhova, Pärnu (EE); Viiu Tuulik, Tallinn (EE); Kaire Aadamsoo, Tallinn (EE); Ülle Võhma, Tallinn (EE)

(73) Assignees: Tallinn University of Technology, Tallinn (EE); North Estonia Medical Centre, Tallinn (EE)

( * ) Notice: Subject to any disclaimer, the term of this patent is extended or adjusted under 35 U.S.C. 154(b) by 994 days.

(21) Appl. No.: 12/196,335

(22) Filed: Aug. 22, 2008

(65) Prior Publication Data

US 2009/0054801 A1    Feb. 26, 2009

Related U.S. Application Data

(60) Provisional application No. 60/957,514, filed on Aug. 23, 2007.

(51) Int. Cl.
*A61B 5/04* (2006.01)
(52) U.S. Cl. .......................................... 600/544
(58) Field of Classification Search .......... 600/300–301, 600/544–545
See application file for complete search history.

(56) References Cited

U.S. PATENT DOCUMENTS

| 5,083,571 | A | * | 1/1992 | Prichep | .......................... 600/544 |
| 5,230,346 | A | | 7/1993 | Leuchter et al. | |
| 6,021,346 | A | | 2/2000 | Ryu et al. | |
| 6,622,036 | B1 | | 9/2003 | Suffin | |
| 2003/0181821 | A1 | * | 9/2003 | Greenwald et al. | .......... 600/544 |

OTHER PUBLICATIONS

Knott et al. EEG power, frequency, asymmetry, and coherence in male depression. Psychiatry Research Neuroimaging. Elsevier Science. Apr. 10, 2001.pp. 123-140.*
Glass and Kwiatokowski. Power Spectral Density Changes in EEG during Mental Arithmetic and Eye-Opening. Pyschol. Forsch. 1970. pp. 85-99.*
Saletu, B. et al., "EEG Mapping and Low-Resolution Brain Electromagnetic Tomography (LORETA) in Diagnosis and Therapy of Psychiatric Disorders: Evidence for a Key-Lock Principle", Clinical EEG and Neuroscience, 2005, pp. 108-115, vol. 36, No. 2.
Knott, V. et al., "EEG Power, Frequency, Asymmetry and Coherence in Male Depression", Psychiatry Research: Neuroimaging, 2001, pp. 123-140, vol. 106.
Allen, J.B. et al., "The Stability of Resting Frontal Electroencephalographic Asymmetry in Depression", Psychophysiology, 2004, pp. 269-280, vol. 41.

(Continued)

*Primary Examiner* — Michael Kahelin
*Assistant Examiner* — Tiffany Weston
(74) *Attorney, Agent, or Firm* — Maine Cernota & Rardin

(57) ABSTRACT

The present invention provides a method and device for determining depressive disorders or other mental disorders related to similar brain imbalances when the combination of powers of specific frequency bands in quantitative EEG has a certain positive or negative value. The present invention performs a signal-processing task to resting EEG recording, calculates the power of two specific frequency bands, finds the combination of the powers and evaluates the result. The method can be used as quick and easy noninvasive tool for diagnosing depression related problems in different patients as separate algorithm, as a part of an EEG recording and analysis device and as a separate device.

17 Claims, 7 Drawing Sheets

OTHER PUBLICATIONS

Flor-Henry, P. et al., "A Source-Imaging (Low-Resolution Electromagnetic Tomography) Study of the EEGs From Unmedicated Males With Depression", Psychiatry Research: Neuroimaging, 2004, pp. 191-207, vol. 130.

Lubar, Joel et al., "Low-Resolution Electromagnetic Tomography (LORETA) of Cerebral Activity in Chronic Depressive Disorder", International Journal of Psychophysiology, 2003, pp. 175-185, vol. 49.

Maltez, J. et al., "Time Course and Variability of Power in Different Frequency Bands of EEG During Resting Conditions", Clinical Neurophysiology, 2004, pp. 195-202, vol. 34.

Rangaswamy, M. et al., "Beta Power in the EEG of Alcoholics", Society of Biological Psychiatry, 2002, pp. 831-842, vol. 52.

Bachmann, M. et al., "Effect of 450 MHz Microwave Modulated with 217 Hz on Human EEG in Rest", The Environmentalist, 2005, pp. 165-171, vol. 25.

Hinrikus, Hiie et al., "Electroencephalographic Spectral Asymmetry Index for Detection of Depression", Med. Biol. Eng. Comput., Mar. 9, 2009, 9 pages.

\* cited by examiner

```
┌─────────────────────────────────────────────┐
│ EEG Signal Recorded as baseline in eyes closed │
│       condition during 20 – 30 min           │
│         Electrode location Parietal          │
└─────────────────────────────────────────────┘
                      │
┌─────────────────────────────────────────────┐
│  Power spectral estimation of the recorded EEG │
│                signal $X(f)$                  │
└─────────────────────────────────────────────┘
                      │
┌─────────────────────────────────────────────┐
│      Finding the central frequency $f_{max}$  │
│  with the maximum power in the subband 8-13 Hz│
└─────────────────────────────────────────────┘
                      │
┌─────────────────────────────────────────────┐
│   Defining a central subband CF of EEG spectrum│
│           $f_{max}$ - 2Hz ... $f_{max}$ + 2Hz │
└─────────────────────────────────────────────┘
                      │
┌─────────────────────────────────────────────┐
│ Calculating the best parabolic fit for the CF subband│
│   of the EEG spectrum and finding the frequency of │
│          the parabol maximum $f_{pmax}$       │
└─────────────────────────────────────────────┘
                      │
┌─────────────────────────────────────────────┐
│   Calculating corrected low (cLF) and high (cHF)│
│          subbands of the EEG spectrum        │
│      $f_{pmax} - 6Hz < cLF < f_{pmax} + 2Hz$ │
│      $f_{pmax} + 2Hz < cHF < f_{pmax} + 26Hz$│
└─────────────────────────────────────────────┘
                      │
┌─────────────────────────────────────────────┐
│  Calculating of Spectral Assymmetry Index as a ratio of│
│  power differences of corrected frequency bands of EEG│
│                   Spectrum                    │
│   $cSASI = [X(f)_{cHF} - X(f)_{cLF}]/X(f)_{cHF} + X(f)_{cLF}]$│
└─────────────────────────────────────────────┘
                      │
┌─────────────────────────────────────────────┐
│ Positive diagnosis of Depressive Disorder if cSASI > 0│
│ Negative diagnosis of Depressive Disorder if cSASI < 0│
└─────────────────────────────────────────────┘
                      │
┌─────────────────────────────────────────────┐
│                     END                      │
└─────────────────────────────────────────────┘
```

FIG. 3

METHOD AND DEVICE FOR DETERMINING DEPRESSIVE DISORDERS BY MEASURING BIOELECTROMAGNETIC SIGNALS OF THE BRAIN

CROSS REFERENCE TO RELATED APPLICATIONS

This application claims the benefit of U.S. provisional patent application No. 60/957,514, filed on Aug. 23, 2007, incorporated herein by reference in its entirety for all purposes.

TECHNICAL FIELD

The invention relates to the field of medical diagnosis and more specifically, to methods and devices for determining mental disorders such as depression by measuring and monitoring the bioelectromagnetic signals of the brain, e.g., by electroencephalogram (EEG).

BACKGROUND OF THE INVENTION

Fast rhythm of life and everyday stress has raised significantly the role of mental diseases and disorders in our society. Depression and other mental disorders are more and more frequent. About 340 million people (6 percent of total population of the world) suffer from deep depression. According to study performed by NIH (National Institute of Health), USA, during last 10 years the number of diagnosed depression increased about 40 times.

Even though depression and other mental disorders are more frequent, the physiological mechanisms of these are not finally clear yet. As a cause of depression, biochemical changes in brain can be considered as disturbance of the function of catecholamines and serotonin in the brain. According to another theory, depression is related to the imbalance of neurotransmitters in brain.

The diagnosis for depression is based on evaluation of the intensity of subjective and clinical symptoms by psychiatrists (M.I.N.I. interview, Hamilton test, and others). Distinguishing reactions to somatic diseases from depressive disorders requiring treatment is very complicated in psychiatric diagnostics. Therefore, there is a great need for methods for determining depression based on objective symptoms. There is a further need for objective monitoring of possible appearance of depressive conditions or other mental disorders of high-risk or high-stress workers such as military personnel, police, rescue workers.

Without doubt, changes in physiological state of the brain do occur together with mental illness and analysis of such changes can provide objective information. Changes in rhythms of bioelectrical activity of the brain, related to the changes in EEG, have been successfully used for diagnosing several neurological and psychiatric diseases (epilepsy, schizophrenia and others). However, only limited data are available about changes in neurophysiological state of the brain in depressive disorders.

Based on previous studies it was supposed that left frontal hypoactivation is distinctive for depressed individuals, being characterized by relatively more left alpha activity [1-4]. Moreover, frontal alpha asymmetry seems to characterize also recovered depressives [1, 3]. The results of the studies showed that EEG alpha asymmetry in depressives demonstrates stability that is comparable in magnitude to that seen in non-clinical populations and the stability is apparent despite rather substantial improvements in clinical state [2].

No relationship between depression severity and EEG asymmetry could be proven [3]. In addition, absolute and relative power in beta band appeared to differentiate patients and controls, with patients exhibiting more power than controls [1]. One of the studies employing LORETA (low-resolution electromagnetic tomography) observed in depressed individuals a pattern of more central, temporal, superior fronto-lateral and medial frontal asymmetry (increased alpha2 current density in the left hemisphere as compared to the right hemisphere) [4], which correlates with previous findings. Decreased current density in delta band was observed in right temporal lobe and the same trend was seen also in theta, alpha and beta band [4].

The results of the other study, employing the same method, showed increased source-current density underlying the EEG from the right hemisphere in the delta, alpha and beta frequency bands both during the resting and cognitively challenged conditions [3]. The expected left anterior hypoactivation in depression (reflected by increased resting left frontal EEG power in the alpha band compared to controls) was not seen [3]. The results suggested exactly the opposite, increased activation of the left frontal lobe and decreased activation of the right frontal lobe. Results showed significantly reduced delta band source-current density in depressed individuals compared to controls during the resting condition in most of the brain volume [3].

The following references were addressed:
[1] V. Knott, C. Mahoney, S. Kennedy, K. Evans, "EEG power, frequency, asymmetry and coherence in male depression," *Psychiatry Research: Neuroimaging*, vol. 106, pp. 123-140, 2001.
[2] J. B. Allen, H. L. Urry, S. K. Hitt, and J. A. Coan, "The stability of resting frontal electroencephalographic asymmetry in depression," *Physiology*, vol. 41, pp. 269-275, 2004.
[3] P. Flor-Henry, J. C. Lind, Z. J. Koles, "A source-imaging (low-resolution electromagnetic tomography) study of the EEGs from unmedicated males with depression," *Psychiatry Research: Neuroimaging*, vol. 109, pp. 191-207, 2004.
[4] J. F. Lubar, M. Congedo, J. H. Askew, "Low-resolution electromagnetic tomography (LORETA) of cerebral activity in chronic depressive disorder," *International Journal of Psychopathology*, vol. 49, pp. 175-185, 2003.

From the review above we can conclude that published results about changes in EEG caused by depression are contradictory and do not allow to make useful conclusions to evaluate the depressive mode.

In U.S. Pat. No. 6,021,346 a method for determining positive and negative emotional states by using a relative power in a subband of a specific frequency band increases or decreases in the course of time. The invention determines positive and negative emotional states by using a relative power in a subband of a specific frequency band increases or decreases with the lapse of time. The invention performs a Fourier transform for a unit time not an entire response time regarding a stimulus, and can be used in real time by using a time-frequency analysis method continuously executed with the lapse of time.

In U.S. Pat. No. 6,622,036, neurophysiologic information such as quantitative electroencephalography is used in a method for classifying, diagnosing, and treating physiologic brain imbalances, including for remotely assessing and treating patients with physiologic brain imbalances.

In U.S. Pat. No. 5,230,346, determining the brain condition of a human between normal and abnormal as determined by dementia, and selectively between dementia of the Alzheimer's-type and multi-infarct dementia is effected. Measures of electrical output, spectral ratio and coherence value of the brain are determined. Selected scores are applied to the electrical output, spectral ratio and coherence values. A relationship between the scores and additionally the scored value of a coherence ratio are effected to obtain a diagnostic evaluation.

Depression has been shown to cause asymmetry and decreased coherence between brain hemispheres. However, published results about depression caused changes in EEG asymmetry are contradictory and cause doubts in hemispheric asymmetry based indicators to evaluate the depressive mode. Nevertheless, subjective symptoms of depression should be accompanied by changes in bioelectrical activity of the brain and in the EEG signal. Comparisons of the EEG signals of healthy persons and patients with depressive disorder may allow to detect characteristic features in the EEG produced by depression and to find objective criteria and measures for evaluation of depression and other mental disorders. By the present invention, there is provided a method and device based on the analysis of combination of the EEG selected bands power for distinction of characteristic features in the EEG caused by depression and other mental disorders.

OBJECTS AND SUMMARY OF THE INVENTIONS

The invented method is based on the notion that combination of the EEG beta and theta band power provides distinction of characteristic features in the EEG caused by depression.

The present invention is directed to a method for determining depressive disorders or other similar brain inbalances from EEG/QEEG (quantative EEG), which substantially obviates the above-described problem due to limitations and disadvantages of the related art. It is an object of the present invention to provide a method for calculating and combining the changes in EEG power at theta and beta frequency bands and to provide parameters characterizing the existence or non-existence of depressive disorder for a subject.

In one embodiment, the method uses an algorithm where different power spectral components of bioelectromagnetic activity signal of the brain are calculated by filtering or by Fourier analysis, namely a spectral asymmetry index (SASI) is calculated from two special frequency bands lower (theta band) and higher (beta band) of the EEG spectrum maximum and excluding central frequency band round EEG spectrum maximum (alpha band) from calculations. The polarity of the index value is the main indicator of the depressive or other mental disorder.

The limiting frequencies of beta and theta band have a role in SASI index calculation and can be defined in different ways. One aspect of the invention is excluding of central (alpha) frequencies from analysis. The limiting frequencies can be fixed or adjusted taking into account alpha frequency range in power spectrum of a particular subject. In last case the parameter is called a corrected spectral asymmetry index (cSASI).

For SASI and cSASI calculation resting EEG recording (eyes closed) is needed, preferably for 10 to 30 minutes. Single channel recording is sufficient for the index calculations. In one embodiment, one of the P channels in international classification system of 10-20-electrode position is used.

The SASI and cSASI calculation algorithms can be used for analysis of recorded EEG data, as a tool for EEG analysis in EEG recording and analyzing device and in a separate wearable device for EEG recording and analysis. The separate wearable device uses at least two electrodes for EEG recordings, amplifier, processor for SASI and cSASI calculations, an indicator-display and a power supply.

It is to be understood that both the foregoing brief description and the following detailed description are exemplary and explanatory and are intended to provide further explanation of the invention as claimed.

BRIEF DESCRIPTION OF THE DRAWINGS

The present invention will become more fully understood from the detailed description given herein below and the accompanying drawings which are given by way of illustration only, and thus are not limitative of the present invention, and wherein:

FIG. 3 is a block diagram of a method for determining depressive disorder by calculating corrected SASI (cSASI).

FIG. 6 is a graph that shows calculated values of SASI for individual subjects in symmetric EEG channels.

FIG. 7 is a graph that shows calculated values of cSASI for individual subjects in symmetric EEG channels.

DETAILED DESCRIPTION OF THE INVENTIONS

Figure 1:
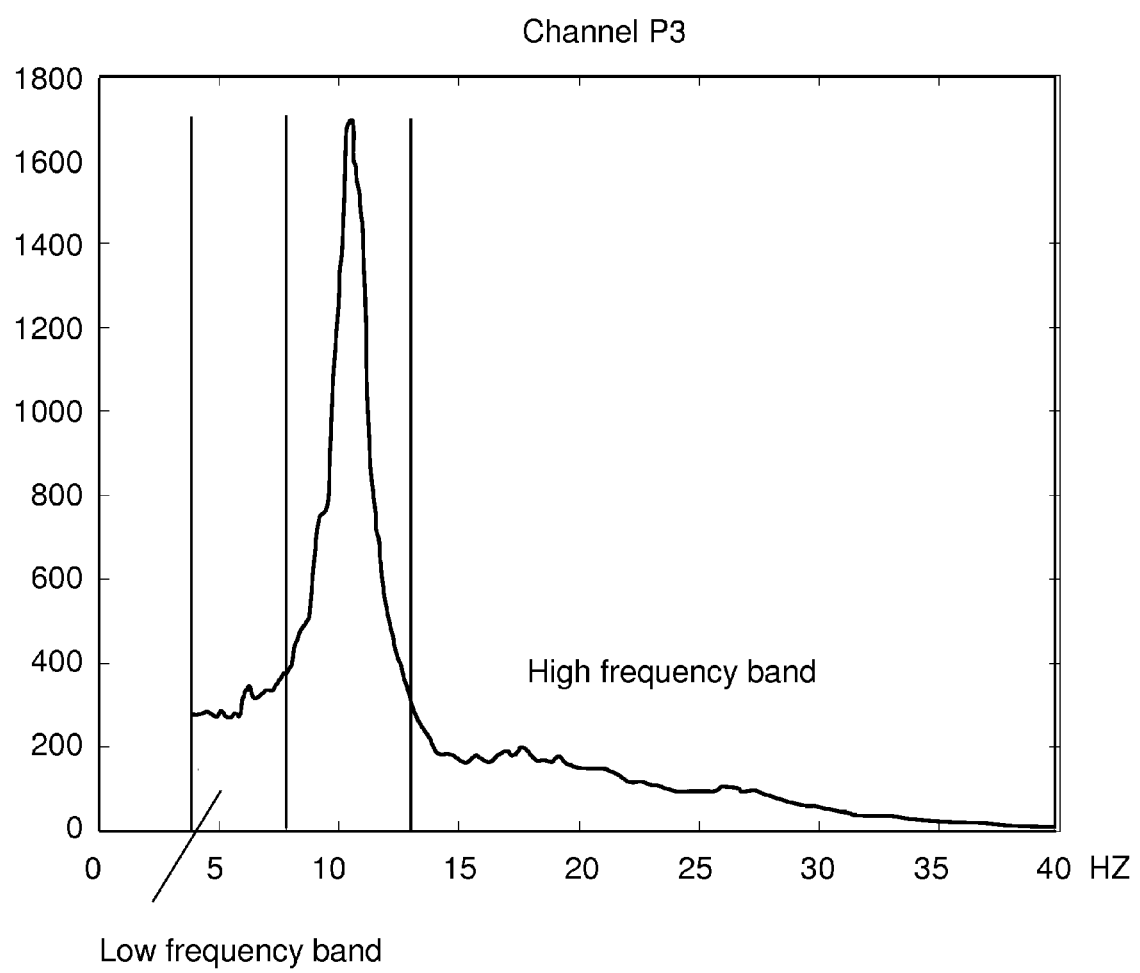
FIG. 1 is an EEG spectrum, showing the locations of higher frequency (beta) and lower frequency (theta) bands according to present invention.
Figure 2:
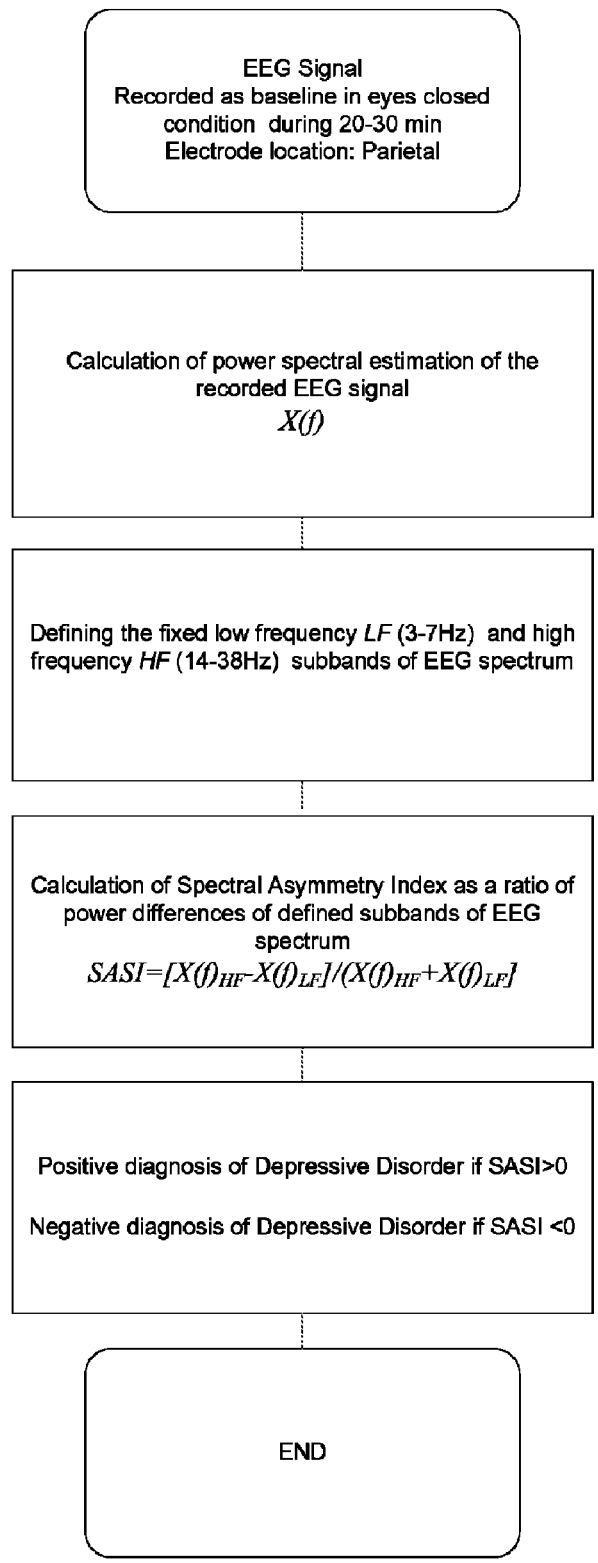
FIG. 2 is a block diagram of a method for determining depressive disorder by calculating SASI.

Reference is now made in detail to the preferred and other embodiments of the present invention, examples of which are illustrated in the accompanying drawings.

The present invention is based on calculating a Spectral Asymmetry Index (SASI) from the power spectra of two frequency bands. The formula can be generally presented as:

$$SASI = \frac{\int_{f_3}^{f_4} X(f)df - \int_{f_1}^{f_2} X(f)df}{\int_{f_3}^{f_4} X(f)df + \int_{f_1}^{f_2} X(f)df}$$

where $X(f)$ is power spectrum of bioelectromagnetic activity signal of the brain (measured by EEG, MEG or others). One of the frequency bands $f_3$ to $f_4$ is selected higher (beta band B, also HF) and the other $f_1$ to $f_2$ is selected lower (theta band T, also LF) than the spectrum maximum of the activity signal of the brain. Values of signal powers within selected bands B and T characterize asymmetry of the spectrum. An important feature defining the B and T bands is excluding central frequency band around spectral maximum (alpha band A, also CF) from the analysis. The precise definition of B and T bands limiting frequencies is performed using several ways. Three embodiments are described here but it is clear that the invention is not limited to these three definitions of band values.

According to one embodiment, the limiting frequencies are chosen as follows: $f_1=4$ Hz, $f_2=7$ Hz, $f_3=14$ Hz and $f_4=38$ Hz for calculating SASI.

According to another embodiment, determining the limiting frequencies for B and T band for a particular subject is based on assumption that often the alpha band of the subject is shifted from its conventional frequencies (low-alpha or high-alpha). In this case a corrected SASI (cSASI) index can be calculated by modifying the frequencies $f_1$, $f_2$, $f_3$, and $f_4$. One possible way is described here. The first step is estimating the frequency with the maximum spectral power $f_{max}$ in the region of 8-13 Hz of the recorded EEG. Thereafter the best parabolic fit is calculated to the $f_{max} \pm 2$ Hz spectrum. The maximum point of the fitted parabola $f_{pmax}$ is taken as a centre value for the alpha band. Reference points for corrected frequency bands (cHF and cLF) for cSASI are determined as follows: $f_1=f_{pmax}-6$ Hz, $f_2=f_{pmax}-2$ Hz, $f_3=f_{pmax}+2$ Hz, $f_4=f_{pmax}+26$ Hz. It should be also understood that this way of excluding alpha frequencies from cSASI calculation is exemplary and different approaches are possible that are still in the scope of current invention.

The third way for determining the limiting frequencies for HF and LF band is based on defining the central frequency band as an alpha frequency band which power significantly decreases when a subject opens eyes. In this case lower frequency $f_3$ of higher frequency band HF is equal to higher limit of decreased EEG power and higher frequency $f_2$ of lower frequency band LF is equal to lower limit of decreased EEG power.

EXAMPLE

The experiments were carried out on two groups of volunteers: a group of patients with major depressive disorder and a group of healthy comparison subjects. Each group consisted of 18 female persons, mean age 39 years, standard deviation 10 years. Subjects with major depressive disorder were selected from hospital inpatient unit. Subjects with non-psychotic major depressive disorder as defined by ICD-10 criteria and determined by 17-item Hamilton Depression Rating Scale (HAM-D) score more than 14 were eligible. The average HAM-D score for the group was 21 (SD 3.3). Subjects were without antidepressant treatment. Concomitant treatments for current general medical conditions were permitted on the basis of clinical judgment (patients receiving medication with known side effects on central nervous system were not eligible). The study was conducted in accordance with the Declaration of Helsinki and was formally approved by the local Medical Research Ethics Committee.

Experimental Protocol and EEG Analysis

The experimental procedure consisted of continuous resting eyes closed EEG recording during 30 minutes. The experimenter and the subjects were in the dark laboratory room during the experiments. The subjects were lying in a relaxed position, eyes closed and ears blocked during the experiments. The Cadwell Easy II EEG measurement equipment was used for the EEG recordings The EEG was recorded using 19 electrodes, which were placed on the subject's head according to the international 10-20-electrode position classification system. The channels for analysis were chosen to cover the entire head: frontal—FP1, FP2; parietal P5, P4; temporal—T3, T4; occipital O1, O2 and the reference electrode Cz. The EEG recordings were stored in a computer using 400 Hz sampling frequency. The power spectral density (PSD) of the recorded EEG signal was estimated by means of Welch's averaged periodogram method. The signal was divided into overlapping sections (50%), with the length of 2048 points and windowed by the Hanning window.

Afterwards, the power in the LF (4-7 Hz) and HF (14-38 Hz) band was computed for each subject as the area under the spectrum for the corresponding frequency band (integral of the band). SASI was calculated for all subjects according to formula above.

Parallel the cSASI was calculated. The frequency of the maximum spectral power $f_{max}$ was estimation in the region of 8-13 Hz. Thereafter the best parabolic fit was calculated to the $f_{max} \pm 2$ Hz spectrum. The maximum point of the fitted parabola $f_{pmax}$ was taken as a centre value of the band CF. Frequency bands HF and LF for cSASI were determined as follows: $f_1=f_{pmax}-6$ Hz, $f_2=f_{pmax}-2$ Hz, $f_3=f_{pmax}+2$ Hz, $f_4=f_{pmax}+26$ Hz.

Parameter cSASI for a subject was calculated according to the formula described above. Signal processing and calculation of parameters were performed in the MatLab and LabVIEW programming and signal processing environment.

Results

Figure 4:
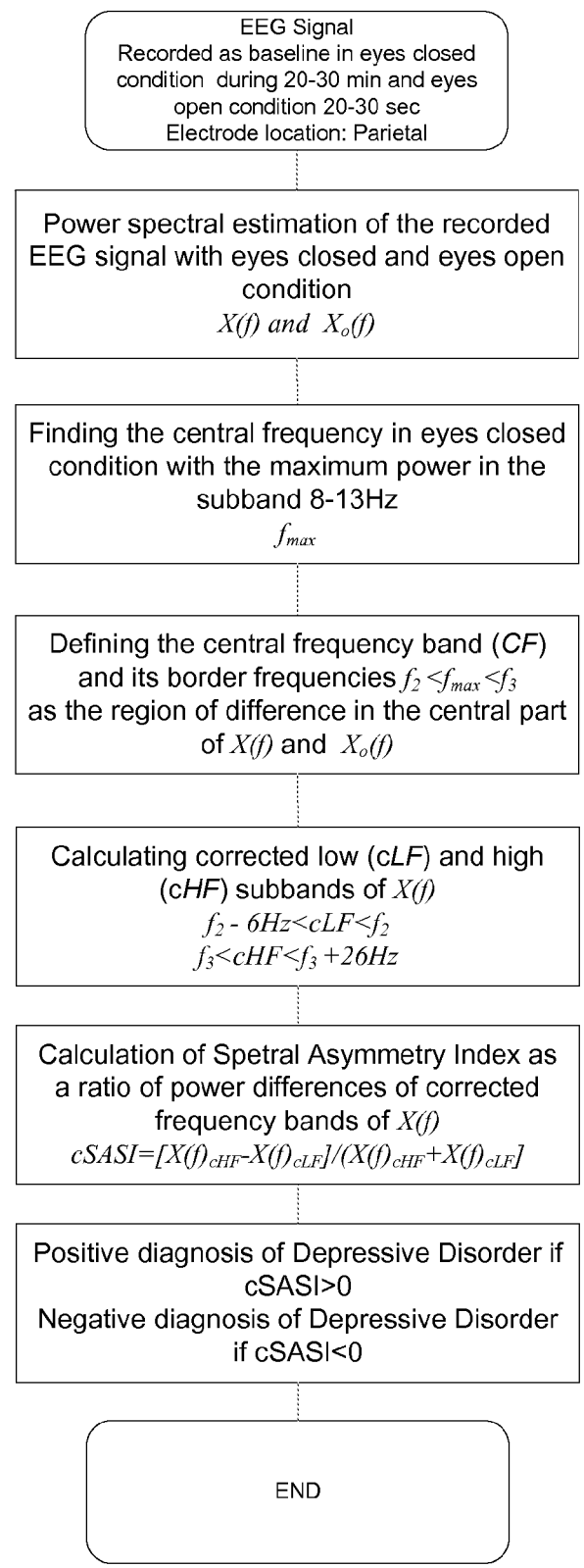
FIG. 4 is a block diagram of a further method for determining depressive disorder by calculating corrected SASI (cSASI).
Figure 5:
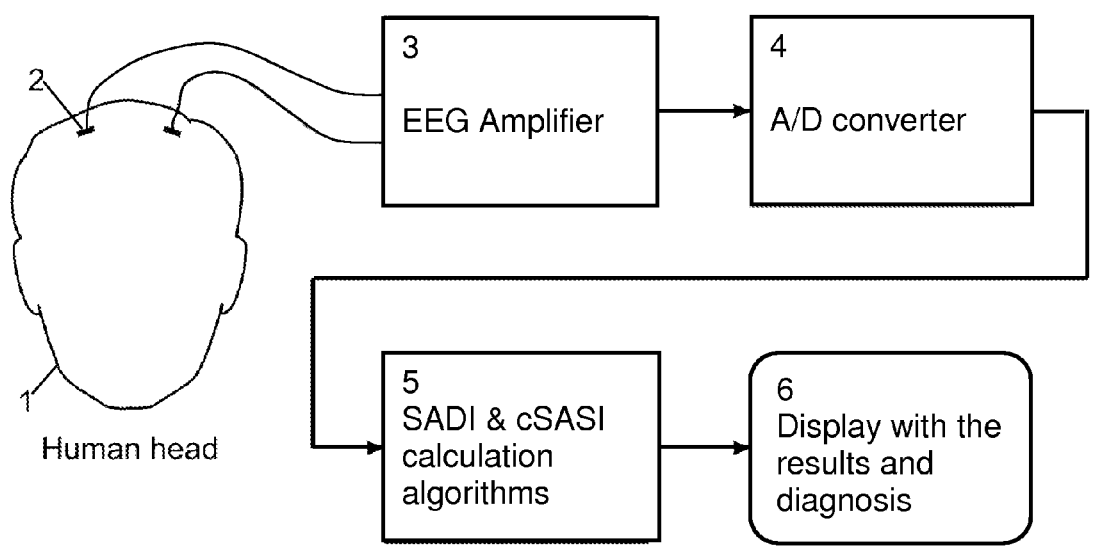
FIG. 5 is a structural scheme of a device for measurement of SASI and cSASI and for determining depressive disorder.

Parameters SASI and cSASI values were calculated in each EEG channel (8) for each subject in the groups of patients with depressive disorder and healthy subjects. Values of SASI and cSASI parameters for each subject in P3 and P4 channels are presented in FIGS. 3 and 4. Results in frontal, temporal and occipital channels were similar. As can be seen from the FIGS. 3 and 4 positive values of SASI prevail for patients with depressive disorder and negative values prevail for healthy subjects.

Hamilton test scores for patients with depressive disorder and values of calculated SASI and cSASI parameters are presented in Table 1.

TABLE 1

Calculated SASI and cSASI values in P3 and P4 EEG channels and Hamilton test scores for patients with depressive disorder.

| SASI | | CSASI | | Hamilton |
| --- | --- | --- | --- | --- |
| P3 | P4 | P3 | P4 | test |
| −0.70976 | −0.74408 | 0.096 | −0.071 | 17 |
| 0.068861 | 0.048907 | 0.117 | 0.182 | 17 |
| 0.344449 | 0.378201 | 0.374 | 0.075 | 20 |
| 0.123771 | 0.118723 | 0.177 | 0.135 | 20 |
| 0.368606 | 0.406663 | 0.410 | 0.443 | 22 |
| 0.149337 | 0.252144 | 0.130 | 0.244 | 22 |
| 0.447907 | 0.442863 | 0.506 | 0.478 | 20 |
| 0.343162 | 0.429961 | 0.310 | 0.372 | 20 |
| 0.129796 | 0.134331 | 0.199 | 0.155 | 22 |
| −0.25406 | −0.18257 | −0.088 | −0.013 | 18 |
| 0.364769 | 0.396001 | 0.243 | 0.261 | 19 |
| 0.484125 | 0.509341 | 0.449 | 0.489 | 24 |
| 0.658612 | 0.649608 | 0.587 | 0.556 | 27 |
| 0.425472 | 0.430825 | 0.444 | 0.445 | 27 |
| 0.776882 | 0.764701 | 0.798 | 0.795 | 26 |
| 0.486627 | 0.45839 | 0.433 | 0.400 | 26 |
| 0.114486 | 0.119744 | 0.227 | 0.200 | 24 |
| 0.229875 | 0.279593 | 0.296 | 0.302 | 22 |

Coefficients of correlation r were calculated between all different parameters in Table 1: between SASI and cSASI parameters, between Hamilton test scores and SASI/cSASI values, between parameters in P3 and P4 channels.

TABLE 2

Calculated correlation coefficients between calculated parameters and Hamilton test scores for patients with depressive disorder

|  | SASI | cSASI | Ham. test | P3 | P4 |
|---|---|---|---|---|---|
| SASI |  | 0.85337 P4 channel | 0.673161 P4 channel |  |  |
| CSASI | 0.842326 P3 channel |  | 0.727817 P4 channel |  |  |
| Ham. test | 0.69724 P3 channel | 0.713079 P3 channel |  |  |  |
| P3 |  |  |  |  | 0.902166 cSASI |
| P4 |  |  |  | 0.993286 SASI |  |

Calculated values of SASI and cSASI parameters are well correlated in two symmetric EEG channels (r>0.9), between themselves (r>0.8) and finally with Hamilton test score (r>0.67 for SASI and r>0.71 for cSASI).

Figure 6A:
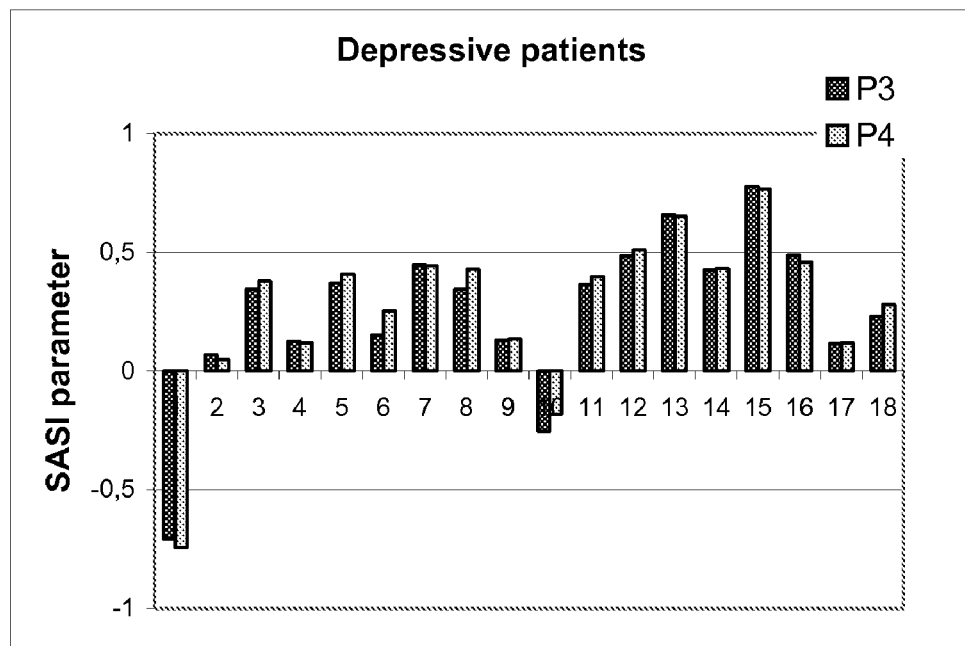
FIG. 6A represents data of 18 patients with clinically diagnosed depressive disorder and FIG. 6B represents data of healthy subjects.
Figure 6B:
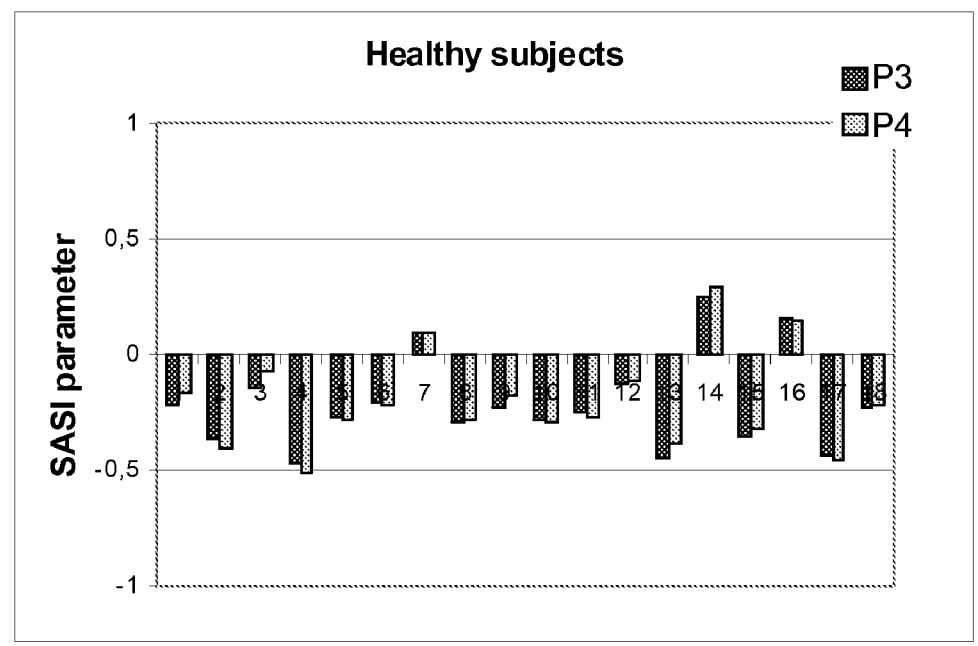
Figure 7A:
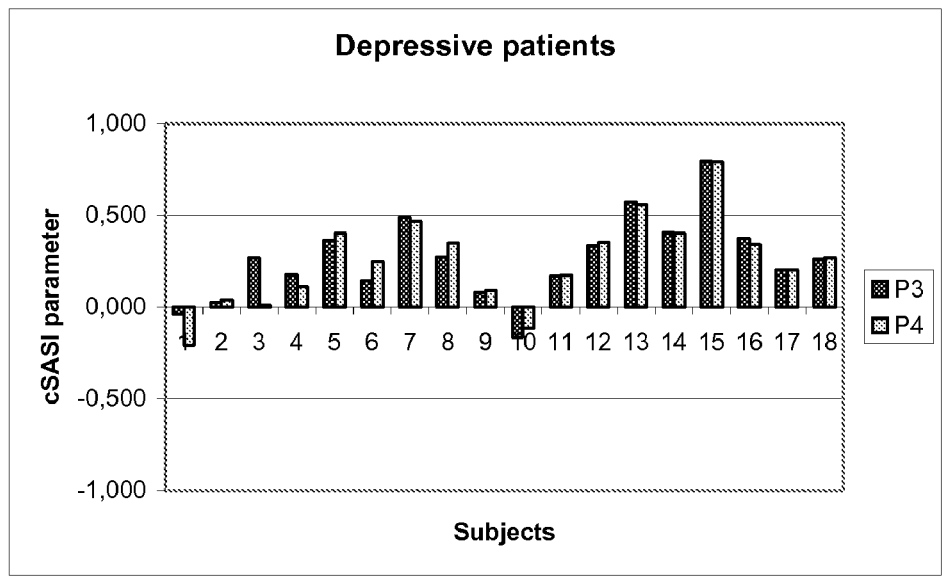
FIG. 7A represents data of 18 patients with clinically diagnosed depressive disorder and FIG. 7B represents data of healthy subjects.
Figure 7B:
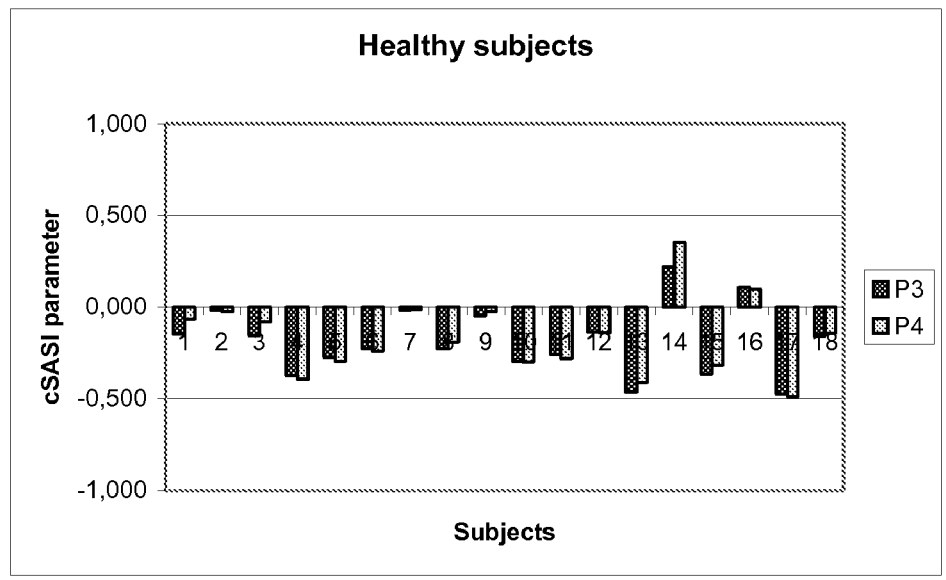

SASI values in two symmetric EEG channels (FIGS. 6 and 7) are close to each other. Statistical comparisons of symmetric channels did not reveal significant differences between hemispheres (p>0.05).

Calculated SASI/cSASI values for depressive and healthy subjects (FIGS. 6 and 7) differ significantly. Two-sample unequal variance t-test for differences between the groups of healthy and depressive subjects resulted in p=1.3 E-7.

The invention claimed is:

1. A method for determining a mental condition of a subject by measuring bioelectromagnetic signals of the brain and calculating a spectral asymmetry index representing the mental condition, the method comprising:
   obtaining a recorded bioelectromagnetic signal from only one site on the subject's brain during a predetermining period of time;
   performing, on a processor, a power spectral calculation on said recorded bioelectromagnetic signal;
   defining a lower frequency band of said bioelectromagnetic signal, said lower frequency band having a second limiting frequency that is below a lower limiting frequency of an alpha band of said bioelectromagnetic signal of the brain, and a first limiting frequency chosen below said second limiting frequency, and calculating a first power of said bioelectromagnetic signal within said lower frequency band;
   defining a higher frequency band of said bioelectromagnetic signal, said higher frequency band having a third limiting frequency that is above a higher limiting frequency of an alpha band of said bioelectromagnetic signal of the brain, and a fourth limiting frequency chosen above said third limiting frequency, and calculating a second power of said bioelectromagnetic signal within said higher frequency band;
   calculating a spectral asymmetry index by subtracting the first power value from the second power value and dividing the result with the sum of the first power value and the second power value; and
   defining a positive determination of the mental condition when the spectral asymmetry index is in the first predetermined range and defining a negative determination of the mental condition when the spectral asymmetry index is in the second predetermined range.

2. The method as in claim 1, wherein said bioelectromagnetic signal is an EEG signal, a quantitative EEG signal, or a MEG signal.

3. The method as in claim 2, wherein said predetermined period of time is from 5 to 30 minutes.

4. The method as in claim 3, wherein said first limiting frequency is about 4 Hz.

5. The method of claim 4, wherein said second limiting frequency is about 7 Hz.

6. The method of claim 5, wherein said third limiting frequency is about 14 Hz.

7. The method of claim 6, wherein said fourth limiting frequency is about 38 Hz.

8. The method of claim 7, wherein said first predetermined range is less than zero and said second predetermined range is larger than zero.

9. The method as in claim 8, wherein said mental condition is a depressive disorder or a mental disorder similar to a depressive disorder.

10. The method as in claim 8, wherein said spectral asymmetry index represents subject's response to a treatment of a mental condition.

11. The method as in claim 1, wherein said spectral asymmetry index represents subject's suitability for inclusion in drug trials.

12. The method as in claim 1, wherein said spectral asymmetry index is used to determine early symptoms of depression or other mental disorders of a subject.

13. The method as in claim 1, wherein said alpha band is a corrected alpha band, said corrected alpha band determined by following steps:
   determining a local maximum frequency in the region of 8 to 13 Hz, corresponding to a maximum of the power spectrum;
   defining said corrected alpha band as having band width 4 Hz, wherein said local maximum frequency is a center frequency of said corrected alpha band;
   calculating a best parabolic fit to said corrected alpha band and taking the maximum point of said best parabolic fit as a corrected center frequency of said corrected alpha band.

14. The method as in claim 13, wherein said first limiting frequency is about 6 Hz less than said corrected center frequency and said second limiting frequency is about 2 Hz less than said corrected center frequency.

15. The method as in claim 14, wherein said third limiting frequency is about 2 Hz more than said corrected center frequency and said fourth limiting frequency is about 26 Hz more than said corrected center frequency.

16. The method as in claim 1, wherein said alpha band is a corrected alpha band, said corrected alpha band determined by the following steps:
   obtaining a second recorded bioelectromagnetic signal from the subject's brain with the patient's eyes open;
   performing a power spectral calculation on said second recorded bioelectromagnetic signal; and
   defining said corrected alpha band as a frequency range where the power significantly decreases for the patient's eyes open compared to the patient's eyes closed.

17. The method as in claim 16, wherein said second limiting frequency is equal to a lower limiting frequency of said corrected alpha band and said first limiting frequency is about 3 Hz less than said second limiting frequency and said third limiting frequency is equal to a higher limiting frequency and fourth limiting frequency is about 24 Hz higher than said third limiting frequency.

* * * * *